Figure 1:
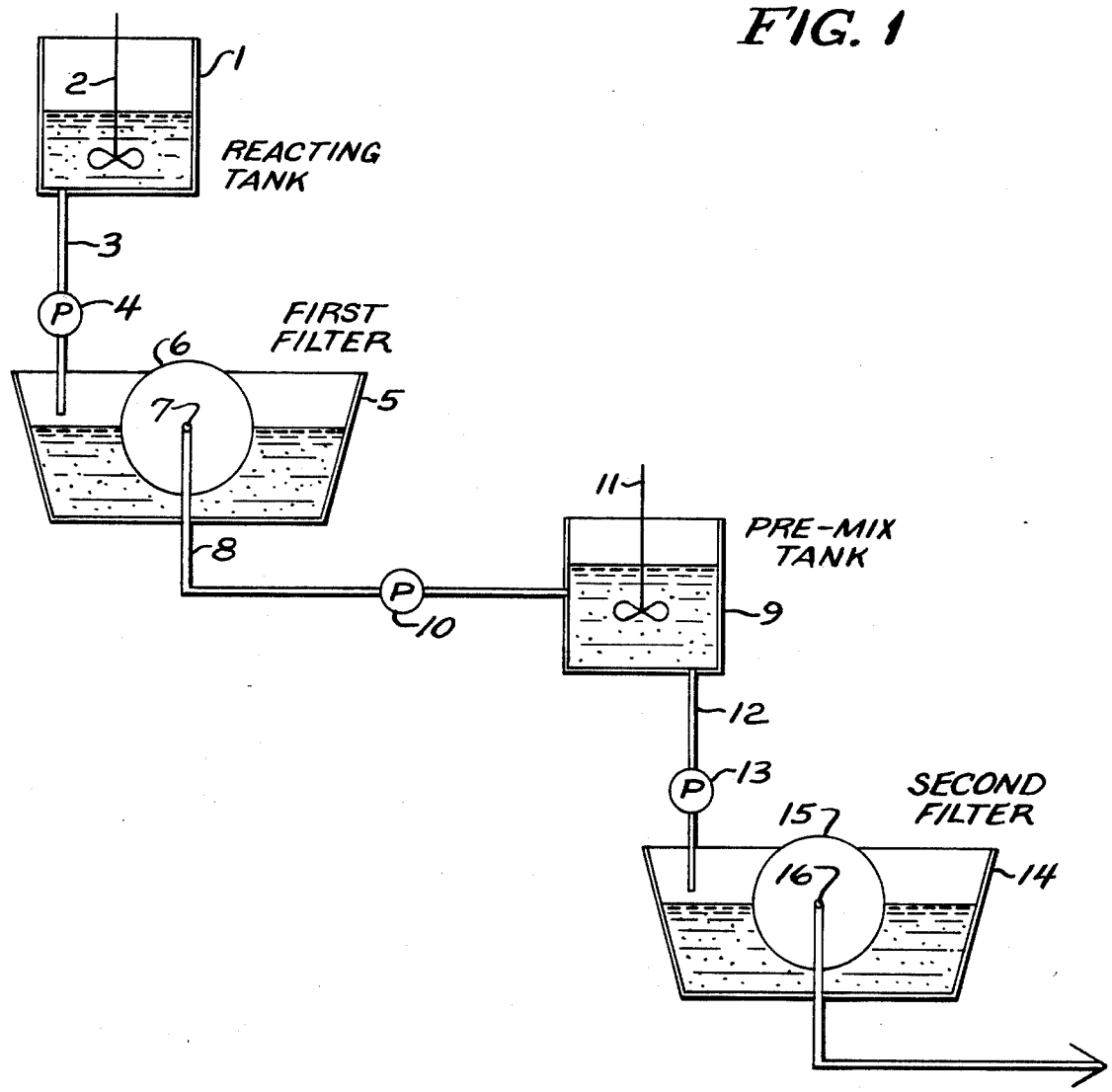

United States Patent [19]

Frank et al.

[11] Patent Number: 4,575,434

[45] Date of Patent: Mar. 11, 1986

[54] PROCESS FOR THE SEPARATION OF AMIDES FROM NITRILES

[75] Inventors: Dieter Frank, Naperville; Lincoln D. Metcalfe, La Grange; John Y. G. Park, Naperville, all of Ill.

[73] Assignee: Akzona Incorporated, Enka, N.C.

[21] Appl. No.: 656,083

[22] Filed: Sep. 28, 1984

[51] Int. Cl.$^4$ .................. C07C 120/08; C07C 121/16
[52] U.S. Cl. .................................... 558/435; 558/467; 260/404
[58] Field of Search .......................... 260/465.2, 465.1

[56] References Cited

U.S. PATENT DOCUMENTS

| | | | |
|---|---|---|---|
| 2,622,097 | 12/1952 | Osborne et al. | 260/465.9 |
| 2,943,049 | 6/1960 | Nahin et al. | 502/11 |
| 3,206,497 | 9/1965 | Oblad | 260/465.2 |
| 3,262,966 | 7/1966 | Higgins, Jr. et al. | 260/465.9 |
| 4,147,717 | 4/1979 | Kershaw | 260/465.8 R |

OTHER PUBLICATIONS

Van Olphen, Clay Colloid Chemistry, 2nd Ed., 1977, (pp. 155–187), Wiley Pub.

*Primary Examiner*—Joseph Paul Brust

*Attorney, Agent, or Firm*—Francis W. Young; Louis A. Morris

[57] ABSTRACT

A process for the removal of impurities comprising amides from a solution comprising nitriles and the impurities. A reaction mixture is formed which includes the solution, a layered mineral comprising aluminum silicates having exchangeable alkaline or alkaline earth cations on the surfaces of the layers and an acid which has an acid strength sufficient to protonate the amides at amide protonation conditions, but in which the solubility of the salt of the acid and exchangeable cation at those conditions is such that the equilibrium of the protonation reaction is substantially in the direction of the amides remaining in a protonated form. The water content of the reaction mixture must be less than about 0.5 wt. % for substantially all of the reaction time. The reaction mixture is maintained for a sufficient time at the amide protonation conditions for protonation of the amides and exchange of the protonated amides and exchangeable cations to occur, the protonated amides adhering to the surfaces of the layers. Nitriles having a reduced content of impurities may then be separated from the reaction mixture. Effective means of separation are rotating drum vacuum filters, preferably two in series.

15 Claims, 4 Drawing Figures

PROCESS FOR THE SEPARATION OF AMIDES FROM NITRILES

BACKGROUND OF THE INVENTION

The field of art to which this invention pertains is the purification of nitriles. Specifically this invention relates to a process for separating impurities comprising amides from nitriles which utilizes an acid and mineral to effect such separation.

BACKGROUND INFORMATION

Nitriles, particularly fatty nitriles, those derived from fatty acids, are important articles of commerce which are useful in the preparation of insecticides, gelling agents, fabric softeners and wetting agents. They may be hydrogenated to form primary, secondary or tertiary amines, particularly the valuable aliphatic amines.

A common commercial method for obtaining nitriles is the catalytic dehydration of fatty acids in the presence of ammonia. This method, however, yields, in addition to the nitriles, many troublesome by products, including different amines which contribute color and odor, and also amides. Such impurities, particularly the amides, must be removed before the nitriles may be used in the various processes which produce the valuable products.

There are many teachings in the prior art that deal with the purification of nitriles, usually by removing those byproducts of the nitrile synthesis reaction, primarily color bodies and amines, which are close in boiling point to the nitrile product and, therefore, difficult to remove by distillation. In the process of U.S. Pat. No. 2,622,097 to Osborne impure acrylonitrile is first passed through activated carbon then through a moistened ion exchange material which may be regenerated by the use of acid, but which is substantially free of acid when used. The process of U.S. Pat. No. 2,943,049 removes hydrocarbon compounds of nitrogen, particularly amines, from hydrocarbon mixtures using various siliceous minerals, including bentonite which have been completely hydrogen ion exchanged. U.S. Pat. No. 3,206,497 to Oblad discloses the separation of a nitrile from a mixture containing other nitrogen-containing compounds of basic character by contacting the mixture with a metal halide which precipitates out the basic nitrogen compound. In the process of U.S. Pat. No. 3,262,966 to Higgins, Jr. et al, activated alumina is used to remove carbonyl compound impurities from acrylonitrile. In the process of U.S. Pat. No. 4,147,717 to Kershaw, amines are removed from adiponitrile by using a variety of materials, including bentonite in the presence of acid, with the adiponitrile preferably containing from 1 to 10% by weight of water. The process of Great Britain Pat. No. 1,223,790 to Kuhlmann effects removal of impurities from nitriles, particularly hetrocyclic compounds containing one or more nitrogen atoms in the ring, by using various adsorbents, including montmorillonite. German Pat. No. 1,046,601 to Cadus et al discloses a process for the purification of adiponitrile using a solid adsorbent such as silica gel, activated carbon or clay.

It is also known to the art that organic cations, particulary amines, may replace cations which were originally present on clay surfaces and that there is a strong preference of the clay for the organic cation. *Clay Colloid Chemistry*, Van Olphen, H., Wiley, 2nd Ed., 1977 is one reference that provides such a teaching.

The present invention addresses a problem not specifically addressed by any of the above references comprising the presence of amides as an impurity in the nitriles. Nitriles produced via the above reaction in which fatty acids are dehydrated in the presence of catalyst and ammonia may contain amides in solution up to the saturation point (about 0.9 wt. % amide). The prior art method for removing these amides has been simple distillation which is sometimes feasible because of the significant difference in boiling points between the nitriles and amides. If one, however, has to work with nitriles of mixed chain lengths, distillative separations may not always be possible due to the fact that the higher boiling amides of the shorter chain length co-distill with the higher chain length nitriles. Distillation, also, requires considerable energy input which in an era of increasing energy costs becomes increasingly unattractive.

We have discovered a process that effects removal of amides from solution with nitriles without employing distillation.

SUMMARY OF THE INVENTION

The primary objective to which the present invention is directed is the removal of amides from a solution of nitriles and amides.

Accordingly, the invention is, in one embodiment, a process for the removal of impurities comprising amides, but which may include other impurities such as amines, from a solution of the nitriles and impurities. A reaction mixture is first formed which includes the solution, a layered mineral comprising aluminum silicates having exchangeable alkaline or alkaline earth cations on the surface of the layers and an acid which has an acid strength sufficient to protonate the amides at amide protonation conditions, but in which the solubility of the salt of the acid and exchangeable cation at those conditions is such that the equilibrium of the protonation reaction is substantially in the direction of the amides remaining in a protonated form. The reaction mixture is maintained for a sufficient time at the amide protonation conditions for protonation of the amides and exchange of the protonated amides and exchangeable cations to occur, the protonated amides adhering to the surfaces of the layers. It is essential for the water content of the reaction mixture to be maintained at less than about 0.5 wt. % for substantially all of the reaction time. Nitriles having a reduced content of impurities may then be separated from the reaction mixture.

Other embodiments of the present invention encompass details about feed mixtures, layered minerals, reactant proportions, choice of acids, separation techniques and operating conditions all of which are hereinafter disclosed in the following discussion of each of the facets of the present invention.

DESCRIPTION OF THE INVENTION

Nitrile feedstocks of primary interest to the present invention fall into one of the three types comprising "coconitrile", "tallow-nitrile" and "oleo-nitrile". The compositions of these types, in terms of percent of fatty nitriles of various chain lengths, are in accordance with the following:

| No. of Carbons | 6 | 8 | 10 | 12 | 14 | 16 | 18 | 14' | 16' | 18' | 18" |
|---|---|---|---|---|---|---|---|---|---|---|---|
| Coco-nitrile | .5 | 8 | 7 | 50 | 18 | 8 | 1.5 | | | 6 | 1 |

| No. of Carbons | 6 | 8 | 10 | 12 | 14 | 16 | 18 | 14' | 16' | 18' | 18" |
|---|---|---|---|---|---|---|---|---|---|---|---|
| Tallow-nitrile | | | | 1 | 3 | 29 | 23 | 1 | 3 | 37 | 1.5 |
| Oleo-nitrile | | | | .5 | 3.5 | 4 | | 5 | 1.5 | 5 | 76 | 3 |

The superscripts ' and " conotate, one unsaturated and two unsaturated bonds respectively, per molecule.

The amide impurity with which the present invention is particularly concerned has the chemical structure:

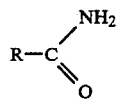

where R may comprise a wide variety of hydrocarbon or hydrocarbon based groups, particularly long chain aliphatics. The reaction mixture of the invention will include such amides, a suitable acid and a layered mineral, such as clay, comprising aluminum silicates having exchangeable alkaline or alkaline earth cations on the surfaces of the layers. The reaction mixture will be hetrogeneous with nitrile, acid and solid phases. The amide content in the nitrile may be as high as its solubility limit (up to about 0.9 wt. % at room temperature) or even greater whereupon at least a portion of the amides would appear as particulate matter. The average molecular weight of the amides in the above feedstock is assumed hereinafter to be 270. Amides of that molecular weight are referred to as "tallow amides".

There may also be a wide variety of other impurities, primarily amines, which may impart color and odor to the nitriles.

Although not limiting the invention to a particular hypothesis, it is believed that the first step in the reaction is the double protonation of the above amide by the acid to produce an ion having the structural formula:

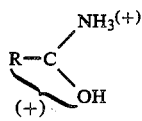

The amide ions will transfer to the acid phase. As the acid phase comes into contact with the layered mineral, the second step of the reaction will occur wherein exchangeable cations on the surfaces of the layers exchange with the amide ions so that the amide ions become associated with the mineral and the exchangeable cations move into the acid phase. At that point a third essential step occurs, the precipitation of acid salts of the exchangeable cation to cause that cation to be removed from the reaction system and in turn ensure the equilibrium of the protonation reaction to be substantially in the direction of the amides remaining in a protonated form and not re-exchange with the exchangeable cations.

The choice of acid to achieve the above is very critical. First, the acid must be strong enough to double protonate the amide, and, second, the solubility of the salt of the acid and exchangeble cation must be such that the above equilibrium effect will occur. Water content of the reaction mixture must be carefully controlled to a value less than about 0.5 wt. % of the reaction mixture for substantially all of the time that the reaction occurs because of the solublizing effects of water. To effect maximum amide removal there should also be an amount of acid in excess of the stoichiometric amount required to effect double protonation of the amides in order to provide a vehicle for the amide and exchangeable ions and because of a portion of the acid being consumed in the course of the various reactions.

The above critical limitations to the present invention may be compared to teachings in the art such as in the above patent to Kershaw, particularly Example XI thereof in which to crude adiponitrile was added bentonite, phosphoric acid and water to effect the removal of MAP, an amine. The quantity of water added (2 ml) comprised about 8.0 wt. % of the reaction mixture. There may or may not have been amides present in this reaction mixture, but if they were present the process of the present invention was not performed, even by serendipity, because, if for no other reason, the quantity of water present was far in excess of that which would have enabled the solubility requirement of the present invention to be achieved.

The conditions at which the process of the present invention is carried out, referred to as the amide protonation conditions, are not critical. A temperature of from about 30° C. to about 100° C. and reaction time from about 30 minutes to about 4 hours are the contemplated normal operating conditions for a fatty nitriles feedstock having carbon chains of from about 10 to about 18 in length. Control of the water content of the reaction mixture is best obtained by maintaining a vacuum pressure of from about 30 to about 150 mm Hg, and more preferably from about 50 to about 75 mm Hg. Of course, as the reaction mixture is being formed the water content may be above the required 0.5 wt. % maximum because of the water content of the clay, acid and even nitrile feed streams, but the vacuum will quickly cause the water to evaporate and thus achieve the required less than about 0.5 wt. % for substantially all of the reaction time.

The vacuum applied to the reaction mixture provides the further advantage of increasing the rate at which the nitriles can be filtered from the mineral, particularly clay, since clay with higher moisture content tends to gel and form cake on filter means (discussed hereafter) which inhibits the filtering rate.

The reaction of the present invention is best carried out by means of a slurry of the mineral and acid in the nitrile-amide solution. Bentonite clay is an excellent source of the mineral and readily disintegrates in a liquid medium to the finely divided particles conducive to slurry formation. The acid, such as sulfuric, should be added to the slurry in the form of fine droplets so as to avoid charring and provide a good initial dispersion. The slurry may be maintained for the course of the reaction by agitating means such as a stirrer or mixer.

A key step in the process of the present invention is the separation of the nitriles having a reduced content of impurities from the reaction mixture. We believe this to be best accomplished by means of one or more vacuum filter assemblies. Such an assembly is basically a filter medium, such as a filter cloth, one side of which, the feedside, is exposed to the fluid to be filtered, and the other side of which, the filtrate side is exposed to a vacuum, thus causing the fluid to be filtered to flow through the multiplicity of openings in the filter medium and, hopefully, the particulate matter to remain on the feed side of the medium. Useful filter cloths may be made of materials such as polyester, polypropylene or teflon, with pore openings, for use in the present invention ranging from about 10 to about 25 microns. The filter may be pre-coated on the feed side with fresh clay to enhance its separation efficiency particularly with regard to fine particulate matter such as amides which have precipitated out of a nitrile feedstock supersaturated with amides.

Rotating vacuum drum filters, such as those manufactured by Bird Young Company, are the most practical commercial scale vacuum filters, at least with regard to the process of the present invention. The rotating vacuum drum filter comprises a feed holding vessel and a rotating vacuum drum having a curved surface comprising the filter medium, i.e. a filter cloth supported on the curved surface of the drum in the slurry. A vacuum is maintained in the drum and the drum is rotated about its longitudinal axis. Filtrate is drawn from the slurry into the drum and exits the drum via a conduit with which the drum is in sealed communication about its longitudinal axis. The filter may be pre-coated by applying it first to a slurry of fresh clay in purified nitrile. In operation, the pre-coating may be maintained at an appropriate thickness by continually cutting off excess clay with a knife a fixed distance from the feed side of the filter medium, but which may oscillate back and forth parallel to the longitudinal axis of the drum.

Reference is now made to FIG. 1 to illustrate the most preferred embodiment of the present invention, particularly with regard to the scheme for separating nitriles from the purification reaction mixture. A slurry is shown in batch reacting tank 1, originally comprising clay, acid, and amide contaminated nitriles, which have been maintained for a time and under conditions appropriate to the process of the present invention, including the use of mixer 2. The reaction is now deemed complete and a batch of filtered and a purified nitrile product is to be recovered.

Slurry is pumped via line 3 and pump 4 from tank 1 into holding vessel 5 of a first vacuum filter assembly. Partially immersed in the slurry in holding vessel 5 is vacuum drum 6, an end view of which is shown, which has a filter cloth about its curved periphery. Drum 6 is rotated about its longitudinal axis 7. A vacuum is drawn in drum 6 and filtrate is drawn from vessel 5, through the filter cloth into vessel 6, and from vessel 6 via conduit 8 with which vessel 6 is in sealed communication.

Conduit 8 empties into pre-mix tank 9 via pump 10 where the nitrile is re-slurried with fresh clay. Mixer 11 facilitates the forming and maintaining of the last mentioned slurry. Slurry is pumped from pre-mix tank 9 via conduit 12 and pump 13 into holding vessel 14 of a second vacuum filter assembly. Partially immersed in the slurry in holding vessel 14 is vacuum drum 15, an end view of which is shown, which has a filter cloth about its curved periphery which may be identical to the filter cloth of the first filter assembly. Drum 15 is rotated about its longitudinal axis 16.

Not shown in FIG. 1 are various details such as the means for drawing vacuums in tank 1 and drums 6 and 15 (e.g. steam ejectors) and various valves and other process equipment. One item particularly worth noting is means, also not shown, by which accumulated particulate matter is continuously removed from the surface of the filter cloths. Adjacent compartmented triangular prism shaped (pie shaped) sections of the drums, the apexes of which are along the longitudinal axis of the drums, are sequentially relieved of vacuum pressure, pressurized to superatmospheric pressure with a gas, preferably air, and then restored to vacuum pressure. The pressurizing gas will flow from the filtrate to the feed side of each portion of curved surface of each section in sequence and blow off the accumulated particulate matter of that section.

Certain best modes of operation of the above preferred filtration embodiment of the present invention have also been determined, at least on a pilot plant scale. The amount of fresh clay added to pre-mix tank 9 is considered optimum with regard to particulate and color removal at about 2 wt. % based on nitrile weight. Clay used for pre-mix prior to the second filtration of the nitriles may be reused by combination with fresh make-up clay to the acid-clay reactor. Polyester medium is recommended for both vacuum drum filters, since it has been found to be structurally unaffected by nitriles and acidic clay, may be used as relatively thin cloths which is conducive to high flow rates and is relatively inexpensive as compared to materials like Teflon. Filtration conditions include about the same temperature as used in the acid-clay treatment and a vacuum pressure on the drum filter units of between 590 mm Hg to 150 mm Hg (abs.).

The following non-limiting examples are presented to illustrate the practice of the present invention and the establishment of the empirical relationships upon which particular preferred embodiments of the present invention are based.

EXAMPLE I

Tests were run to determine the effect of the vacuum pressure required for the practice of the present invention for two different nitrile feedstocks. In all tests for this and other examples herein, unless otherwise stated, the source of mineral was a calcium bentonite clay acquired from American Colloid Company, known as "Panther Creek Catalyst Grade" and having the following composition and properties:

| | |
|---|---|
| Composition: | Hydrous silicate of alumina composed principally of the clay mineral montmorillonite. Montmorillonite content 85% minimum. Contains small portions of feldspar, biotite, selenite, etc. |
| Chemical Composition: | Typical Analysis (Moisture Free): |

| | | |
|---|---|---|
| Silica | 56.00–59.00% | as $SiO_2$ |
| Alumina | 18.00–21.00% | as $Al_2O_3$ |
| Iron (Ferric) | 5.00–8.50% | as $Fe_2O_3$ |
| Iron (Ferrous) | 0.37–0.65% | as $FeO$ |
| Magnesium | 3.00–3.30% | as $MgO$ |
| Sodium & Potassium | 0.84–1.25% | as $Na_2O$ |
| Calcium | 1.20–3.50% | as $CaO$ |
| Titanium | 0.80–0.86% | as $TiO_2$ |
| Carbon | 0.45–1.20% | as $CO_2$ |
| Sulfur | 0.09–0.16% | as $SO_2$ |
| Crystal Water | 5.00–6.00% | as $H_2O$ |

| | |
|---|---|
| Chemical Formula: | A tri-layer expanding mineral structure of approximately: $(Al, Fe_{1.67}, Mg_{0.33}) Si_4O_{10}(OH)_2 Na^+ Ca^{++}_{0.33}$ |
| Moisture Content: | Maximum 12% as shipped. |
| Dry Particle Size: | Minimum 80% finer than 200 mesh (74 micron). |

Seven tests were run in a bench scale reactor with the acid (98% $H_2SO_4$) sprayed into a slurry of impure fatty nitrile and clay and the reaction mixture maintained for 30 minutes for each run. Tests 1 through 3 were run with coco-nitrile having an amide content of 0.46 wt %, and UV and Gardener colors of 124 and 7, respectively. Gardner color is a standard color index used throughout the industry, while UV color is an ultra-violet color determination at 420 nanometers wavelength with the UV value of a control sample comprising a nitrile having 0.75 wt. % amide content and 7.5 Gardner color defined as 100. Tests 4 and 5 were run with tallow-nitrile having an amide content of 0.39 wt. % and UV and Gardner colors of 97 and 6, respectively. Tests 6 and 7 were run with oleo-nitrile having an amide content of 0.43 wt. % and UV and Gardner colors of 63 and 5.5, respectively. Following the reaction for each run, each batch was filtered through standard laboratory filter paper in a Buchner funnel having a filter area of 38.5 cm$^2$ and a clay pre-coating 0.5 cm thick. The data obtained is set forth in Table 1.

TABLE 1

| Exp. No. | Batch Temp. °C. | Batch Press. mm Hg. | $H_2SO_4$ Wt. % B.O. Nitrile | Clay wt. % B.O. Nitrile | Filtration Rate | Results % Amide | Color | U.V. Scan |
|---|---|---|---|---|---|---|---|---|
| 1 | 65 | atm. | 0.4 | 4 | 207 g/9 min | 0.1 | G = 1.5 | 10 |
| 2 | 64 | 74.2 | 0.4 | 4 | 208 g/1.8 min | 0.06 | APHA 100 | 10 |
| 3 | 63 | 74.2 | 0.4 | 4 | 218 g/2.9 min | <0.05 | APHA 100 | 9 |
| 4 | 51 | atm. | 0.4 | 4 | 312 g/32 min | 0.11 | G = 3 | 25 |
| 5 | 51 | 74.2 | 0.4 | 4 | 470 g/31 min | 0.11 | G = 2 | 15 |
| 6 | 50 | atm. | 0.4 | 4 | Not available | 0.23 | G = 4 | 34 |
| 7 | 50 | 74.2 | 0.4 | 4 | 300 g/23 min | 0.15 | G = 3 | 18 |

It is important to first note that the moisture contents of the reaction mixtures for each run at atmospheric pressure is calculated to be about 0.98 wt. % based on the water content of the clay, acid and nitrile, as provided, while that of the reaction mixtures at 74.2 mm Hg is calculated to be about 0.32 wt. %.

The effect of water content of the reaction mixture on the test results, with one exception, is dramatic for a given feedstream. With the feed of runs 1 through 3 there is about a 50% reduction in amides and a marked reduction in color (APHA is another standard color index with approximately 100 APHA units equalling 1 Gardner unit). In runs 4 and 5 there was no apparent amide reduction with the vacuum system, but this is deemed attributable to experimental error, such as in analysis of the product sample, since there is no rational reason for the invention to be ineffective for the particular feed used.

In all cases, the vacuum provided improved results with regard to at least one of the color indexes and marked improvements in filtration rates at least for those feeds in which the filtration data was complete.

EXAMPLE II

Tests were run to determine the relative amounts of acid and mineral required for the practice of the present invention for various amounts of amide to be removed from the nitrile feedstock. As discussed above, the amount of acid supplied to the reaction mixture was in excess of the stoichiometric amount required to effect double protonation of the amides. From experimental evidence (Table 3 below) one has to conclude that only the most acidic proton of the respective acid can be used for protonation of the amide. The stoichiometric amount thus would be two moles of acid per mole of amide, but an excess is desired to provide a vehicle for the protonated amides and to make up for the amount of acid consumed.

A series of tests similar to those of Example I were run on a tallow-nitrile feedstock containing 0.75 wt. % amide impurities, a UV scan of 100% and Gardner color of 7.5. The reaction conditions included 60° C. and 74.2 mm Hg pressure. The amounts of sulfuric acid and/or Panther Creek bentonite clay were varied between runs. The data obtained is as set forth in Table 2. All percentages shown are based on the weight of nitriles.

TABLE 2

| Exp. No. | % Clay | % $H_2SO_4$ | Product Analysis % Amide | Color | UV Scan | Δ % Amide Removed |
|---|---|---|---|---|---|---|
| 1 | 4 | 0.25 | 0.280 | G = 1$^+$ | 15 | 0.450 |
| 2 | 4 | 0.50 | 0.255 | G = 2$^+$ | 31 | 0.475 |
| 3 | 4 | 0.75 | 0.325 | G = 2$^+$ | 35 | 0.405 |
| 4 | 5 | 0.25 | 0.20 | G = 1 | 13 | 0.53 |
| 5 | 5 | 0.50 | 0.19 | G = 2 | 25 | 0.54 |
| 6 | 5 | 0.75 | 0.22 | G = 2 | 22 | 0.51 |
| 7 | 5 | 1.00 | 0.27 | G = 2.5 | 28 | 0.46 |
| 8 | 6 | 0.25 | 0.22 | G = 1 | 11 | 0.51 |
| 9 | 6 | 0.50 | 0.16 | G = 1 | 8 | 0.57 |
| 10 | 6 | 0.75 | 0.16 | G = 1 | 10 | 0.57 |
| 11 | 6 | 1.00 | 0.17 | G = 1 | 11 | 0.56 |
| 12 | 7 | 0.25 | 0.15 | APHA = 90 | 10 | 0.58 |
| 13 | 7 | 0.50 | 0.12 | APHA = 90 | 7 | 0.61 |
| 14 | 7 | 0.75 | 0.12 | G = 1 | 8 | 0.61 |
| 15 | 7 | 1.00 | 0.12 | G = 1 | 6 | 0.61 |
| 16 | 7 | 1.25 | 0.13 | G = 1 | 13 | 0.60 |
| 17 | 8 | 0.25 | 0.25 | G = 1 | 12 | 0.48 |
| 18 | 8 | 0.50 | 0.12 | G = 1 | 6 | 0.61 |
| 19 | 8 | 0.75 | 0.09 | G = 1 | 8 | 0.64 |
| 20 | 8 | 1.00 | 0.10 | G = 1 | 8 | 0.63 |
| 21 | 8 | 1.25 | 0.12 | G = 1 | 8 | 0.61 |
| 22 | 8 | 1.50 | 0.11 | G = 1 | 9 | 0.62 |

Figure 2:
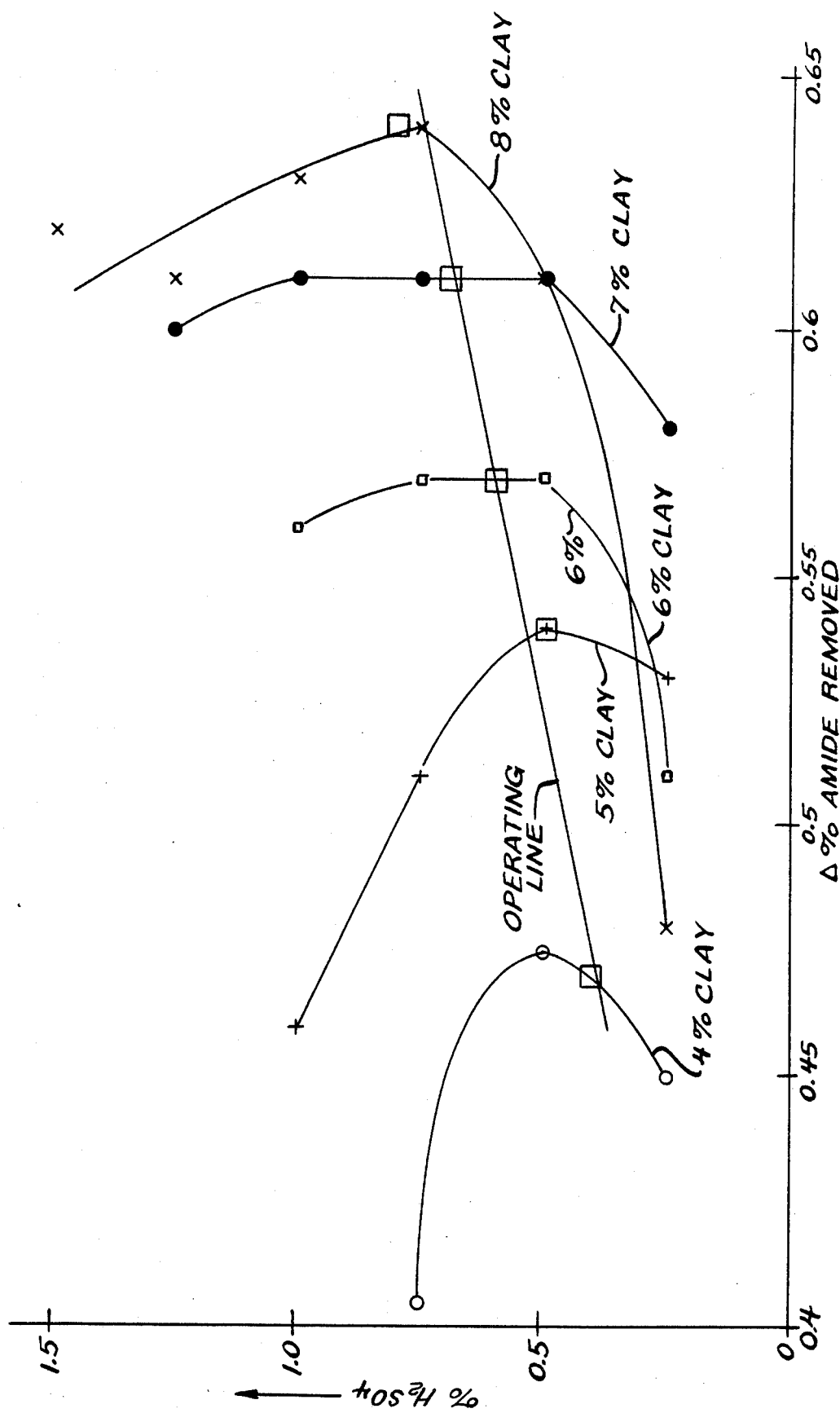

The data of Table 2 (excluding color data) is plotted as FIG. 2 and appears as series of parabolas, one for each level of clay. It may be generally observed from Table 2 and FIG. 2 that as the amount of clay and acid used increases, the amount of amide removed increases and the color indexes decrease. Qualitatively then, it is apparent that the present invention is effective in removing amides from nitriles as well as color bodies which are known to be amines. The latter is surprising in view of the teachings of the prior art concerned with amine removal that relatively high water content in the reaction mixture is required with an acid-clay treatment.

Furthermore, the very interesting observation can be made, particularly from FIG. 2, for a given clay level, that the amount of amide removed will increase with acid concentration to a maximum value and then actually decrease as the acid concentration continues to rise. This is attributable to the excess free acid causing desorption from the clay of previously adsorbed protonated amide. For the range investigated, a single approximately straight line may be drawn through the maximum amide removal point of the curve for each clay level, hereinafter referred to as the "operating line". As will be shown later this operating line may be more exactly fitted to a parabolic equation.

Figure 3:
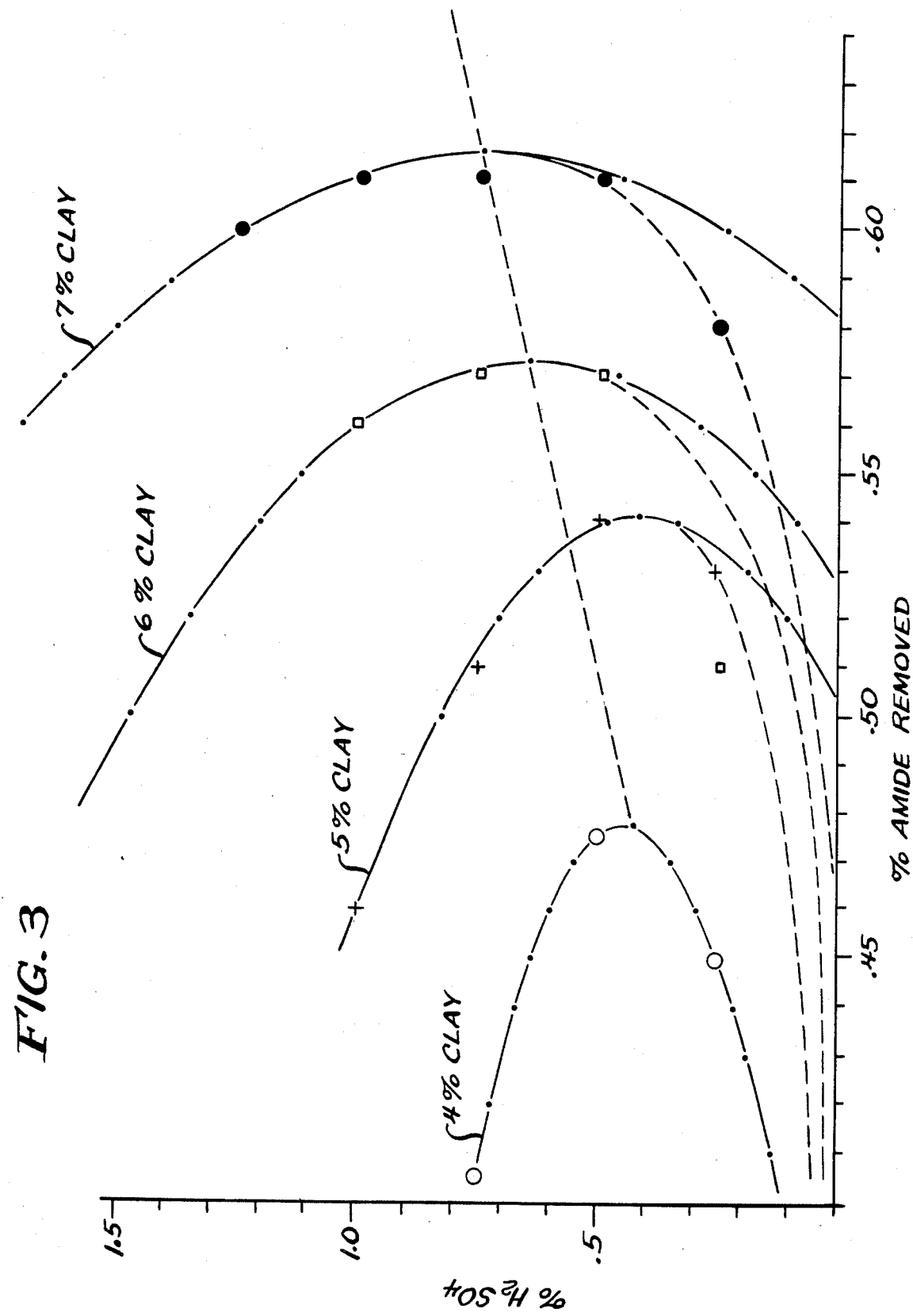

FIG. 2 was replotted as FIG. 3 with the scatter of FIG. 2 eliminated and the curves of FIG. 3 were fitted to parabolic equations. The solid lines in FIG. 3 are the best fits according to the following mathematical expressions:

For 4% clay: $Ac = 0.44 \pm \sqrt{0.640 - 1.343 \cdot AR}$

For 5% clay: $Ac = 0.41 \pm \sqrt{2.325 - 4.298 \cdot AR}$

For 6% clay: $Ac = 0.65 \pm \sqrt{5.399 - 9.423 \cdot AR}$

For 7% clay: $Ac = 0.75 \pm \sqrt{10.250 - 16.667 \cdot AR}$ where
Ac=sulfuric acid used in terms of wt. % of nitrile
AR=amide removed in terms of wt. % of nitrile The experimental data points of Table 2 fit well if above the operating line. Below that line, however, empirical curves have to be drawn as dotted lines. This is no contradiction in itself as two different mechanisms are involved on either side of the operating line. Up to the operating line, increasing amounts of acid at a given clay level remove increasing amounts of amide. Beyond the operating line more acid removes ever increasing amounts of previously adsorbed amide from the clay, thus showing apparent lower percentages of amide removal.

From the data of Table 2 and from the above parabolic equations the following calculated data is presented as Table 3. The prefix "m" as used throughout the specification means "milli" or "thousandths". The term "ideal", as applied to the amounts of acid used, applies to the values calculated from the parabolic equations.

of acid, with the ratio of acid to amide required increasing with the amount of amide to be removed.

It is worthwhile to obtain an approximation of the amount of acid that would be required for a given level of amide desired to be removed. The operating line of FIG. 3 is considered the best such approximation available. The equation of the operating line of FIG. 3 in terms of m moles of acid required vs m mole of amide removed, assuming the above ratio of 2 moles of acid per 2 equivalents of exchangeable cations, would be:

$$Ac = 2.08A^2 - 1.46A + 0.35$$

where
Ac=m moles of acid; and
A=m moles amide to be removed. The plot of this equation over the range of Δ% amide removed shown in FIG. 3 deviates little from a straight line. The term "m moles amide to be removed" may be any amount up to and including the starting amide level, although it is unlikely the process will remove the 100% of the starting amide content. One wishing to operate the process of the present invention would thus know, first, from the last stated equation, approximately how much acid would be required for a given desired level of amide removal, and, second, from the fixed ratio of clay to acid, established by the above experimentation, how much clay is needed. Of course, the operating line of FIG. 3 is specific to a calcium cation and sulfuric acid system, it being understood that other cation-acid combinations would produce a similar set of curves and operating line.

EXAMPLE III

Although the data for the above Examples was obtained with the "Panther Creek" bentonite clay, it

TABLE 3

| Clay wt % | Exchangeable Cation (Ca) Mole | Acid (H₂SO₄) m Mole Observed | Acid (H₂SO₄) m Mole Ideal | Amide Removed m Mole | Ca/AR* | Acid/AR | Acid/Ca |
|---|---|---|---|---|---|---|---|
| 4 | 2.24 | 4.2 | 4.3 | 1.77 | 1.26 | 2.42 | 1.92 |
| 5 | 2.80 | 3.5 | 5.7 | 2.00 | 1.40 | 2.85 | 2.03 |
| 6 | 3.36 | 5.0 | 6.5 | 2.11 | 1.59 | 3.08 | 1.93 |
| 7 | 3.92 | 5.0 | 7.5 | 2.26 | 1.73 | 3.31 | 1.91 |
| 8 | 4.48 | 7.5 | 8.5 | 2.37 | 1.89 | 3.58 | 1.89 |

*Amide removed

Quantitatively, several observations may be made from FIG. 3 and Table 3. First of all, the optimum weight ratio of clay to acid for all levels of clay added appears to be about 10:1 (based on an added clay and acid water content of 12 and 2 wt. %, respectively), which in terms of the mole ratio of acid to equivalents of exchangeable cations is about 2.0:2.0. The latter ratio indicates that it is primarily the first proton from each sulfuric acid molecule that is protonating the amides, i.e. the dissociation constant of the first proton ($pk_a = -3.0$) enhances its availability to protonate the amide as compared to that of the second proton ($pk_a = 1.9$) which is far more difficult to dissociate from the acid.

Another observation is that the actually observed mole ratio of acid to amide removed varies from 2.37 at the 4% clay level to 3.16 at the 8% clay level. The theoretical stoichiometric mole ratio of sulfuric acid to amide should be about 2.0:1.0. Maximum amide removal at given clay level, therefore, requires an excess should be again emphasized that any layered mineral having exchangeable alkaline or alkaline earth cations on its surfaces will serve the purpose. For example, the following Table 4 sets forth the exchangeable cation compositions (as given by the manufacturers) of various commercially available clays.

TABLE 4

| Clay | wt. % CaO | wt. % Na₂O |
|---|---|---|
| Ca Bentonite (USA)[1] | 1.2–3.5 | 8.4–1.25 |
| Colclay H-90[2] | 2.7 | 2.7 |
| Bentonite N (Ca)[3] | 3.93 | 1.6 |
| Bentonite ARB (Na)[4] | not available | not available |
| Colclay A-90 (Na)[5] | .4 | 2.0 |

[1] Panther Creek Bentonite
[2,5] Settimio Cinicola, Vermeer/Milano
[3,4] Societe Francaise des Bentonites et Derives
[3] is natural calcium bentonite 7C "N"
[4] is activated sodium bentonite 7C "ARB"

Each of the above clays was used in accordance with the present invention to remove amides from a nitrile feed comprising tallow-nitrile and 0.36 wt. % amides. In all cases the amount of clay added was 6 wt. % based on nitriles and the clay/acid weight ratio was 10.0:1.0. Reaction conditions included a temperature of 60° C., a pressure of 74.2 mm Hg and a reaction time of 30 min. The results in terms of the analysis of the nitrile product are as set forth in Table 5.

TABLE 5

| Clay | % Amide in Nitriles | % Amide Removed | Relative Amide Removal (%) |
|---|---|---|---|
| Ca—Bentonite (USA) (Ca) | .1 | >.26 | 72 |
| Colclay H-90 (Ca) | .13 | .23 | 64 |
| Bentonite N (Ca) | .14 | .22 | 61 |
| Bentonite ARB (Na) | .15 | .21 | 58 |
| Colclay A-90 (Na) | .16 | .20 | 56 |

The data in Table 5 indicates that clays having sodium cations as the predominate exchangeable cation are also effective to a certain degree for use in the present invention. Direct comparisons of the different clays in their ability to effect amide removal, however, should be in the light that the different clays have different exchangeable cation contents, and that high calcium content in general is more beneficial for high desired amide removals.

EXAMPLE IV

Since a basic premise of the present invention is that the nature of the acid used and the solubility of its exchangeable cation salts are important parameters in the process, a series of experiments were run with four acids which significantly differed in their acid strength as well as the solubilities of their respective salts. Reaction conditions included a temperature of 60° C., a pressure of 74.2 mm Hg and a reaction time of 30 min. and equal molar ratios of acid to exchangeable cations. The results obtained are as set forth in Table 6.

TABLE 6

| | Amide Removal Using Various Acids | | | | Amide Removal wt. % (based on nitriles) | |
|---|---|---|---|---|---|---|
| Acid | MW | Acid Concentration (Wt. %) | Acid/Clay %/% | m Moles Acid | 0.36 ← Starting → 0.65 Amides Wt. % | |
| $H_2SO_4$ | 98 | 98 | 0.6/6 | 6.0 | 0.30 | 0.57 |
| Trichloroacetic (TCA) | 162 | 98 | 1.0/6 | 6.0 | 0.26 | 0.43 |
| $H_3PO_4$ | 98 | 86 | 0.68/6 | 6.0 | 0.24 | 0.32 |
| Benzenesulfonic Monohydrate (BSA) | 158 | 98 | 1.07/6 | 6.0 | 0.21 | 0.22 |

Certain observations should be made at this point concerning the protonation of amides. Such protonation is known in the literature to occur when extremely strong acids are being used, as the protonated amide itself acts as a very strong "conjugated acid" having a pka value of −1 or −0.5 (literature values differ somewhat).

For the four acids used $pk_a$ values were found to be:

| | 1st | 2nd | 3rd | Proton |
|---|---|---|---|---|
| $H_2SO_4$ | −3 | 1.9 | | |
| TCA | 0.9 | | | |
| $H_3PO_4$ | 2.1 | 7.2 | 12.7 | |
| BSA | 0.7 | | | |

For the aforementioned reasons only those protons are available for amide protonation whose $pk_a$ are sufficiently low or close to the $pk_a$ of the protonated amide.

Listing the above acids in descending order of their acid strength, we have:

| | 1st | | 2nd | 3rd | "Average" |
|---|---|---|---|---|---|
| $H_2SO_4$ | −3 | and | 1.9 | | −0.55 |
| BSA | 0.7 | | | | 0.7 |
| TCA | 0.9 | | | | 0.9 |
| $H_3PO_4$ | 2.1 | | 7.2 | 12.7 | 2.1 |

It is re-emphasized here that although the second proton of sulfuric acid in these mechanistic considerations do not significantly contribute to protonation, the $pk_a$ of the second proton has been included in the "average" $pk_a$. On the other hand, the "average" $pk_a$ for $H_3PO_4$ is deemed to be the same as the $pk_a$ of its first proton because the second and third protons are deemed to not contribute whatsoever to the acid strength for purposes of the present invention.

Amide removal, however, does not follow this pattern of acid strength. This effect is even more pronounced when nitrile of higher original amide content is being used and is therefore a true phenomenon and not experimental scatter.

If one now assumes that amide removal follows the mechanics suggested earlier, the acid with highest acid strength and lowest solubility of its calcium salt should exhibit the best amide removal. This is indeed the case as shown in Table 7, which reiterates the results of Table 6. The solubility of the Ca Salt is expressed in terms of grams per 100 grams of water which is considered an appropriate indicator of the solubility of the salt in the acid phase.

TABLE 7

Amide Removal by Various Acids

| Acid | $pk_a$ | Solubility of Ca—salt g/100 g $H_2O$ | Amide Removal from 0.36% starting nitrile % |
|---|---|---|---|
| $H_2SO_4$ | −0.55 | 0.2 | 0.3 |
| TCA | 0.9 | 1.0 | 0.26 |
| $H_3PO_4$ | 2.1 | 1.8 | 0.24 |
| BSA | 0.7 | 61 | 0.21 |

From the experimental data, an expression was derived combining $pk_a$, solubility of the acid salt of the exchangeable cation and amide removal. The first item to be determined is the amount of clay to be present per 100 grams of nitrile. Such amount for the purposes of this determination may be expressed in terms of the amount required to provide an amount of exchangeable cations per 100 grams of nitrile determined by the following equation:

$$M = 2.08A^2 - 1.46A + 0.35$$

where

M=m mole equivalents of exchangeable cations the clay; and 3
A=m moles of amide to be removed.

Figure 4:
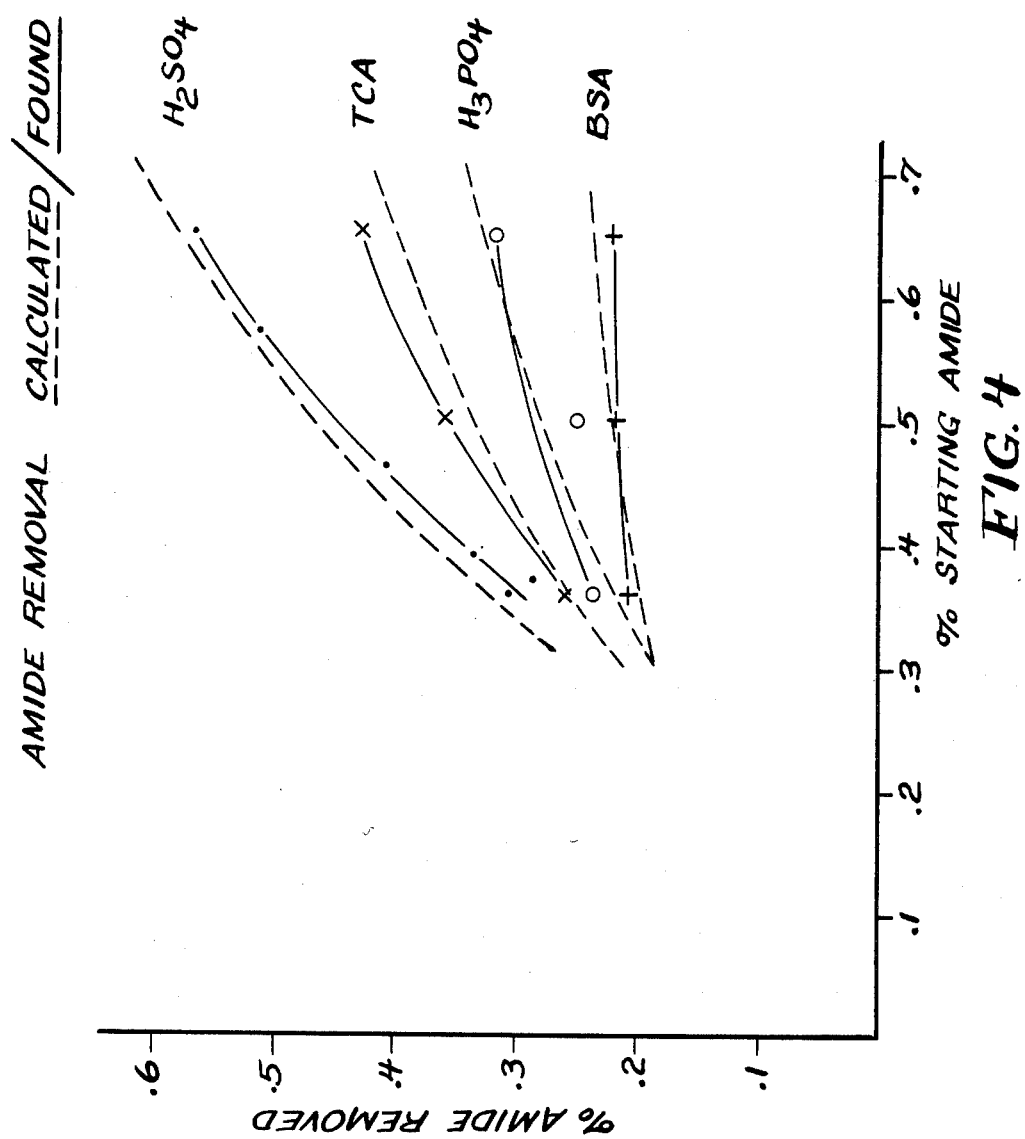

The selection of acid may now be in terms of those acids which achieve a desired degree of amide removal, assuming a mole ratio of acid to equivalent of exchangeable cations of about 2:0:2.0, in accordance with the equation:

$$AR = .1105 \sqrt[3]{\frac{E \cdot \Delta pk_a}{C}} \cdot \log_{10}\left(\frac{A_o}{.36}\right) + .022 \cdot \Delta pk_a + .075 \cdot \sqrt[6]{\frac{E}{C}}$$

where
AR=amount of amide removed as wt. % of nitrile;
$\Delta pk_a$=7−$\log_{10}$ of the reciprocal of the average dissociation constant of the acid as defined on page 26);
Ao=starting amide level as wt. % of nitrile
E=gram equivalent weight of the exchangeable cations;
C=solubility of the acid anion salt of the exchangeable cations in gr./100 gr. water The above derived equation is an excellent fit of the experimental data as is evident from the following Table 8 and FIG. 4.

TABLE 8

Amide Removal by Various Acids

| Acid | Total AR Calculated | | AR Found | |
|------|---------|---------|---------|---------|
|      | .36% Ao | 0.6% Ao | .36% Ao | 0.6% Ao |
| $H_2SO_4$ | 0.327 | 0.55 | 0.30 | 0.5 |
| TCA  | 0.257 | 0.38 | 0.26 | 0.41 |
| $H_3PO_4$ | 0.219 | 0.31 | 0.24 | 0.31 |
| BSA  | 0.200 | 0.23 | 0.21 | 0.22 |

This empirically found equation is not limited to clays with Calcium as the predominant exchangeable cation. As shown in Table 4 when Colclay A-90 was used (0.4% CaO, 2.0% $Na_2O$) an amide removal of 0.20% was found experimentally for a starting amide of 0.36%. The solubility C of sodium sulfate decahydrate is reported to be 93 grams/100 gr. water. Using the equation for this system yields a calculated amide removal of 0.219% which is also in good agreement with the experiment.

EXAMPLE V

The purpose of this example is to illustrate the practice of the present invention in a preferred embodiment as shown in the flow scheme of FIG. 1.

550 lbs. of tallow-nitrile of typical composition as shown earlier (Example I, tests 4 and 5) with an amide content of 0.38% and Gardener color of 5.5 were treated in a stirred reactor (stirrer at 300 RPM) at 60° C. and 74 mm Hg abs. pressure with 7% Calcium Bentonite clay (Panther Creek 12% moisture) and 0.7% of 98% concentrated sulfuric acid which was added to the slurry of clay in nitrile over a period of 10 to 15 min. through a submersed spray nozzle. After an additional agitation time of 30 min. the acidic clay/nitrile slurry was immediately filtered through a rotary drum vacuum filter (Bird Young 5 ft² total surface area) covered with a polyester filter cloth (Tetko Inc., Elmsford, N.Y.; HD7-17μ) at an average vacuum applied of 200 mm Hg. Accumulated clay filter cake was continuously removed from the filter drum by applying air pressure from the inside of the drum to the cake discharge section of the rotating filter drum, sequentially to adjacent pie-shaped compartmented sections of the drum. The filtration rate for the nitrile was 35.7 gal/ft² hr. as an average.

This first filtrate was fed to a second agitated vessel where 2 wt. % of fresh neutral clay were added. After 20 minutes of mixing at 60° C. this slurry was filtered warm through an identical rotary drum vacuum filter covered with a polyester filter cloth (Tetko, Inc., Elmsford, N.Y. HD7-10μ) at a suction pressure of 240 mm Hg an average filtration rate of 32.8 gal/ft² hr. was observed. Cake discharge was achieved exactly as described in the first filtration step.

The so purified tallow-nitrile was a clear liquid, free of mal odor, having a Gardner color <1 and containing <0.1% by weight of the amide impurity.

What we claim is:

1. A process for the removal of long-chain aliphatic amides from a solution of said amides and fatty acid derived nitriles comprising forming a reaction mixture comprising said solution, a layered mineral comprising an aluminum silicate having exchangeable alkaline or alkaline earth cations on the surfaces of said layers and an acid having an acid strength sufficient to protonate said amides at conditions including a temperature of from about 30° C. to about 100° C., a time from about 30 minutes to about 4 hours and a water content in said reaction mixture of less than about 0.5 wt. % for substantially all of said time, the protonated amides adhering to said surface of said layers during said time, the solublity of the salt of said acid and exchangeable cation at said conditions being such that there will be a precipitation of said salt from said reaction mixture, and separating said nitriles having a reduced content of said amides from said reaction mixture.

2. The process of claim 1 wherein said mineral comprises a bentonite clay, and said reaction mixture is in the form of a slurry of finely divided particles of said clay with said solution and acid.

3. The process of claim 2 wherein the moisture content of said slurry is maintained by subjecting said slurry to a vacuum pressure of from about 30 to about 150 mm Hg.

4. The process of claim 2 wherein the amount of clay present is about the amount required to provide a mole ratio of Zacid to equivalents of exchangeable cations of about 2.0:2.0.

5. The process of claim 2 wherein said acid is selected from the group consisting of sulfuric acid, trichloroacetic acid, and phosphoric acid.

6. The process of claim 2 wherein said acid is added to said slurry in the form of fine droplets.

7. The process of claim 4 wherein said exchangeable cations comprise calcium cations, said acid comprises sulfuric acid and the amount of acid provided for a given amount of amide to be removed per 100 gr. of nitrile is approximated by the equation:

$$Ac = 2.08A^2 - 1.46A + 0.35$$

where
Ac=m moles of acid; and
A=m moles of amide to be removed.

8. The process of claim 2 wherein the amount of said clay in said slurry is sufficient to provide an amount of exchangeable cations per 100 grams of nitrile determined by the equation:

$$M = 2.08A^2 - 1.46A + 0.35$$

where
M = m mole equivalents of exchangeable cations in said clay; and
A = m moles of amide to be removed;
the amount of said acid being the amount required to provide a mole ratio of acid to equivalents of exchangeable cations of about 2:0:2.0, said acid being selected from those acids which achieve a desired degree of amide removal in accordance with the equation:

$$AR = .1105 \sqrt[3]{\frac{E \cdot \Delta pk_a}{C}} \cdot \log_{10}\left(\frac{Ao}{.36}\right) + .022 \cdot \Delta pk_a + .075 \cdot \sqrt[6]{\frac{E}{C}}$$

where
AR = amount of amide removed as wt. % of nitrile;
$\Delta pk_a$ = 7-$\log_{10}$ of the reciprocal of the average dissociation constant of the acid;
Ao = starting amide level as wt. % of nitrile;
E = gram equivalent weight of the exchangeable cations; and
C = solubility of the acid anion salt of the exchangeable cations in g/100 g water.

9. The process of claim 2 wherein said clay comprises a calcium bentonite having a tri-layer expanding mineral structure of approximately (Al, Fe$_{1.67}$, Mg$_{0.33}$) Si$_4$O$_{10}$ (OH)$_2$Na+CA+ +0.33.

10. The process of claim 9 wherein said acid comprises sulfuric acid.

11. The process of claim 10 wherein the weight ratio of clay to acid is about 10.0:1.0 on the basis of said clay containing about 12 wt. % water and said acid containing about 2 wt. % water.

12. The process of claim 2 wherein said separation is effected by the method comprising pre-coating the feed side of a vacuum filter with fresh clay, said filter comprising a filter medium having a feed side and a filtrate side and a multiplicity of openings through which the filtered liquid may pass, contacting said slurry with said coated feed side and recovering said nitriles from the filtrate side of said filter.

13. The process of claim 12 wherein said filter comprises a rotating vacuum drum having a curved surface comprising said filter mediam, a portion of said curved surface being immersed in said slurry, the precoating of said clay on said feed side of said filter being maintained at an appropriate thickness by continually cutting off the excess clay with a knife in a fixed distance from the feed side of said filter medium.

14. The process of claim 2 wherein said separation is effected by the method comprising maintaining said slurry in a first vessel, passing said slurry to the feed holding vessel of a first rotating drum vacuum filter, immersing a portion of the curved surface of the rotating vacuum drum in said slurry, said curved surface of said drum comprising a filter medium having a feed side and a filtrate side and a multiplicity of openings through which the filtered liquid may pass but through which a substantial portion of the particulate material in said slurry may not pass, recovering said nitriles from said first rotating vacuum drum, reslurring said nitriles with fresh clay to form a second slurry, passing said second slurry to the feed holding vessel of a second vacuum filter, immersing a portion of the curved surface of the rotating vacuum drum of said second vacuum filter in said second slurry, said curved surface of said drum comprising a filter mediam substantially identical to that of said first vacuum filter, said second filter removing substantially all of the remaining particulate matter in said second slurry, and recovering from said second filter a filtrate comprising nitriles of substantially reduced impurities and particulate matter content.

15. The process of claim 14 wherein accumulated particulate matter is continuously removed from the feed side of each rotating vacuum drum filter by removing the vacuum, pressurizing the inside and re-applying the vacuum sequentially to adjacent compartmented triangular prism shaped sections of said drums, the apexes of which sections are along the longitudinal axis of said drums and the bases of which are portions of the curved surfaces of said drums, said pressuring being effected with a gas at super-atmospheric pressure so as to cause said gas to flow from the filtrate to the feed side of each said section and to blow off said accumulated particulate matter from said feed side of the curved surface of each said section.

* * * * *